United States Patent
Suganuma et al.

(10) Patent No.: US 8,580,550 B2
(45) Date of Patent: Nov. 12, 2013

(54) LIPASE POWDER, METHOD FOR MANUFACTURE THEREOF, AND USE THEREOF

(75) Inventors: Tomomi Suganuma, Yokosuka (JP); Tadashiro Hirose, Yokosuka (JP); Junko Suzuki, Yokosuka (JP); Shin Arimoto, Yokosuka (JP); Hideaki Maki, Yokosuka (JP); Satoshi Negishi, Yokosuka (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 0 days.

(21) Appl. No.: 11/716,580

(22) Filed: Mar. 12, 2007

(65) Prior Publication Data

US 2007/0155003 A1    Jul. 5, 2007

Related U.S. Application Data

(63) Continuation of application No. PCT/JP2005/017125, filed on Sep. 16, 2005.

(30) Foreign Application Priority Data

Sep. 16, 2004    (JP) .................................. 2004-269976

(51) Int. Cl.
  *C12N 9/20*    (2006.01)
(52) U.S. Cl.
  USPC ........................................................ 435/198
(58) Field of Classification Search
  None
  See application file for complete search history.

(56) References Cited

U.S. PATENT DOCUMENTS

| | | | |
|---|---|---|---|
| 4,798,793 A | | 1/1989 | Eigtved |
| 5,156,963 A | * | 10/1992 | Eigtved .......................... 435/135 |
| 5,288,619 A | * | 2/1994 | Brown et al. .................. 435/134 |
| 5,304,477 A | | 4/1994 | Nagoh et al. |
| 5,480,787 A | * | 1/1996 | Negishi et al. ................ 435/134 |
| 5,902,738 A | * | 5/1999 | Orsat et al. .................... 435/155 |
| 6,399,059 B1 | | 6/2002 | Minoshima et al. |
| 2003/0054509 A1 | * | 3/2003 | Lee et al. ....................... 435/134 |
| 2003/0185939 A1 | * | 10/2003 | Nielsen .............................. 426/61 |
| 2003/0199069 A1 | * | 10/2003 | Fuglsang et al. .............. 435/198 |
| 2004/0082056 A1 | * | 4/2004 | Jump et al. ..................... 435/263 |

FOREIGN PATENT DOCUMENTS

| | | |
|---|---|---|
| JP | 04-234985 A | 8/1992 |
| JP | 10-204494 A | 8/1998 |
| TW | 305880 | 5/1997 |

OTHER PUBLICATIONS

Sharma et al. (2001) Biotechnology Advances 19(8): 627-662.*
International Search Report for PCT/JP2005/017125 dated Dec. 6, 2005.
Korean Office Action mailed on Feb. 29, 2012, issued in corresponding Korean Application 9-5-2012-012280473.
Taiwan Official Action issued Jun. 28, 2011, in Taiwanese application 094132152.
Taiwan Official Action issued Sep. 24, 2012, in Taiwanese application 094132152.

* cited by examiner

*Primary Examiner* — Lisa J Hobbs
(74) *Attorney, Agent, or Firm* — Buchanan Ingersoll & Rooney PC

(57) ABSTRACT

There is provided a lipase powder which is a granulated material comprising a lipase and at least one member selected from the group consisting of fatty acids having 8 to 12 carbon atoms, alcohol esters thereof, and a mixture thereof. This lipase powder has an increased lipase activity.

8 Claims, No Drawings

LIPASE POWDER, METHOD FOR MANUFACTURE THEREOF, AND USE THEREOF

TECHNICAL FIELD

The present invention relates to a lipase powder that can be advantageously used for various esterification, transesterification reactions and the like, a method for manufacture thereof, and an esterification method, a transesterification method using such a lipase powder or the like.

BACKGROUND OF THE INVENTION

Lipases have been widely used for esterification of various carboxylic acids such as fatty acids with alcohols such as monoalcohols or polyhydric alcohols and for transesterification between a plurality of carboxylic acid esters. Among those reactions, transesterification is an important technology employed primarily for the modification of animal and vegetable oils and fats and as a method for the manufacture of esters of various fatty acids, sugar esters, or steroids. If a lipase, which is an oils and fats hydrolase, is used as a catalyst for those reactions, the transesterification can be conducted under thermally mild conditions of room temperature to about 70° C., and side reactions can be inhibited and energy cost can be reduced by comparison with the conventional chemical reactions. Moreover, because the lipase serving as a catalyst is a natural product, safety is high. Furthermore, the target product can be manufactured with good efficiency by the mass specificity or position specificity thereof However, if a lipase powder is directly used for transesterification, sufficient activity thereof cannot be demonstrated and it is inherently difficult to disperse a water-soluble lipase in oily starting materials and the recovery thereof is also difficult. For this reason, the lipase has been generally used for esterification or transesterification after immobilizing it on a support, for example, an anion-exchange resin (Patent Document 1), a phenol-adsorbed resin (Patent Document 2), a hydrophilic support (Patent Document 3), a cation-exchange resin (Patent Document 4), and a chelate resin (Patent Document 5).

Lipase has thus been conventionally used for transesterification in an immobilized form, but the immobilizing treatment conducted to obtain such an immobilized lipase resulted in loss of activity inherent to lipase. Moreover, when a porous substrate was used, the pores were clogged by the starting material or reaction products which resulted in the decreased transesterification ratio. Furthermore, in the conventional transesterification reactions using immobilized lipase, moisture held by the support was introduced into the reaction system. As a result, side reactions, for example, the formation of diglycerides or monoglycerides in the transesterification of oils and fats was difficult to avoid.

In light of the foregoing circumstances, a variety of technologies using lipase powders have been developed. For example, there was suggested a method for conducting transesterification in which a lipase powder was dispersed in a starting material containing an ester so that 90% or more of the particles of the dispersed lipase powder had a particle size within a range of 1 to 100 μm during transesterification in the presence or absence of an inert organic solvent (Patent Document 6). Furthermore, it was also suggested to use an enzyme powder obtained by drying an enzyme solution containing a phospholipid or a lipophilic vitamin (Patent Document 7).

However, a lipase powder with even higher lipase activity is desired.

Patent Document 1: Japanese Patent Application laid-open No. S60-98984
Patent Document 2: Japanese Patent Application Laid-open No. S61-202688
Patent Document 3: Japanese Patent Application Laid-open No. H2-138986
Patent Document 4: Japanese Patent Application Laid-open No. H3-61485
Patent Document 5: Japanese Patent Application Laid-open No. H1-262795
Patent Document 6: Japanese Patent No. 2668187
Patent Document 7: Japanese Patent Application Laid-open No. 2000-106873

DISCLOSURE OF THE INVENTION

It is an object of the present invention to provide a lipase powder with increased lipase activity.

Another object of the present invention is to provide a method for the manufacture of the aforementioned lipase powder.

Yet another object of the present invention is to provide an esterification method and a transesterification method using the aforementioned lipase powder.

Those and other objects of the present invention will become clear from the following description.

The present invention is based on the discovery that when a lipase is granulated by using a medium-chain fatty acid, an alcohol ester thereof, or a mixture thereof to obtain a powder form, the lipase activity is increased substantially.

Thus, the present invention provides a lipase powder which is a granulated material comprising a lipase and at least one member selected from the group consisting of fatty acids having 8 to 12 carbon atoms, alcohol esters thereof, and a mixture thereof. The present invention also provides a method for the manufacture of a lipase powder comprising the steps of adding at least one member selected from the group consisting of fatty acids having 8 to 12 carbon atoms, alcohol esters thereof, and a mixture thereof to an aqueous solution containing a lipase and spray-drying or freeze-drying the resulting solution.

The present invention also provides a lipase for esterification or transesterification comprising the aforementioned lipase powder.

The present invention also provides an esterification method of fatty acids and alcohols or a transesterification method, which comprises using the aforementioned lipase powder.

DESCRIPTION OF THE PREFERRED EMBODIMENTS

Examples of lipases that can be used in the present invention include lipoprotein lipase, monoacylglycerolipase, diacylglycerolipase, triacylglycerolipase, galactolipase, and phospholipase. Among them, triacylglycerolipase is preferred.

No specific limitation is placed on microorganisms for producing those lipases and they may be bacteria, yeast, filamentous fungi, and actinomyces, specific examples including *Pseudomonas* sp., *Alcaligenes* sp., *Arthrohacter* sp., *Staphylococcus* sp., *Torulopsis* sp., *Escherichia* sp., *Micotorula* sp., *Propionibacterum* sp., *Chromobacterum* sp., *Xanthomonas* sp., *Lactobacillus* sp., *Clostridium* sp., *Candida* sp., *Geotrichum* sp., *Sacchromycopsis* sp., *Nocardia* sp.,

*Fuzarium* sp., *Aspergillus* sp., *Penicillum* sp., *Mucor* sp., *Rhizopus* sp., *Phycomycese* sp., *Puccinia* sp., *Bacillus* sp., and *Streptmycese* sp.

In the present invention, among them, 1,3-specific lipases are preferred, 1,3-specific lipases derived from *Mucor* sp. or *Alcaligenes* sp. are especially preferred, and 1,3-specific lipases derived from *Rhizomucor miehei* and *Alcaligenes* sp. are even more preferred.

Saturated, unsaturated, linear, and branched fatty acids can be used as the fatty acid having 8 to 12 carbon atoms that is used for the granulation of the lipase in the present invention. Among them saturated fatty acids are preferred, fatty acids having 8 to 10 carbon atoms are even more preferred, and saturated fatty acids having 8 or 10 carbon atoms are especially preferred. Those acids can be used individually or in combinations of two or more thereof. Furthermore, part of the fatty acid may form a salt with an alkali metal or an alkaline earth metal. Among them, a salt with an alkali metal such as sodium or potassium is preferred.

Examples of alcohol esters thereof include esters of the aforementioned fatty acids with various alcohols, for example, monoalcohols, polyhydric alcohols, or mixtures thereof. Examples of the alcohols include glycols such as ethylene glycol, propylene glycol, and butylene glycol, glycerin, erythritol, pentaerythritol, and trimethylolpropane. Among them, partial esters having at least one alcoholic hydroxyl group are preferred. Among them, monoglycerides and diglycerides are preferred and monoglycerides are especially preferred. Those can be used individually or in combinations of two or more thereof.

In the present invention, the aforementioned fatty acids and alcohol esters thereof can be also used together.

The lipase and fatty acid etc. (at least one member selected from the group consisting of fatty acids having 8 to 12 carbon atoms, alcohol esters thereof, and a mixture thereof will be sometimes referred to as "fatty acid etc.") can be used at various ratios, but the amount of the fatty acid etc. being 0.1-20 times the mass of the lipase is preferred, and the amount of 1-20 times is even more preferred.

The moisture content of the lipase powder in the present invention is preferably 10 wt. % or less, more preferably 6.5-8.5 wt. %.

The lipase powder in the present invention can have any particle size, but it is preferred that 90 wt. % or more of the lipase powder have a particle size of 1-100 μm. Furthermore, it is preferred than the particles of the lipase powder have a spherical shape.

The diameter of the lipase powder can be measured, for example, with a particle size distribution meter (LA-500) manufactured by HORIBA Co.

The lipase powder in the present invention can be obtained, for example, by adding a fatty acid etc. to an aqueous solution containing a lipase and then spray drying or freeze drying the resultant.

Here, examples of aqueous solutions containing a lipase include a lipase culture solution from which fungus bodies have been removed, a purified culture solution, solutions obtained by again dissolving or dispersing the lipase powder obtained from the aforementioned solution in water, solutions obtained by again dissolving and dispersing commercial lipase powders in waster, and commercial liquid lipases. Furthermore, in order to further increase the lipase activity, it is more preferred that low-molecular weight components such as salts be removed, and in order to further improve the powder properties, it is more preferred that low-molecular weight components such as sugars be removed.

Examples of lipase culture solutions include aqueous solutions containing soybean powder, peptones, corn steep liquor, $K_2HPO_4$, $(NH_4)_2SO_4$, $MgSO_4 \cdot 7H_2O$ and the like. The concentration thereof can be as follows: soybean powder 0.1-20 wt. %, preferably 1.0-10 wt. %, peptones 0.1-30 wt. %, preferably 0.5-10 wt. %, corn steep liquor 0.1-30 wt. %, preferably 0.5-10 wt. %, $K_2HPO_4$ 0.01-20 wt. %, preferably 0.5-10 wt. %, $(NH_4)_2SO_4$ 0.01-20 wt. %, preferably 0.1-5 wt. %, and $MgSO_4 \cdot 7H_2O$ 0.01-20 wt. %, preferably 0.05-5 wt. %. The culturing conditions can be controlled as follows: culture temperature 10-40° C., preferably 20-35 C., aeration rate 0.1-2.0 VVM, preferably 0.1-1.5 VVM, stirring rotation rate 100-800 rpm, preferably 200-400 rpm, and pH 3.0-10.0, preferably 4.0-9.5.

Separation of fungus bodies may be conducted by centrifugal separation or membrane filtration. Furthermore, removal of low-molecular weight components such as salts and sugars can be conducted by UF membrane treatment. More specifically, an aqueous solution containing lipase from which low-molecular weight components have been removed can be obtained by repeating 1-5 times the operation of concentrating an aqueous solution containing a lipase to ½ volume thereof by conducting UF membrane treatment and then adding a phosphoric acid buffer in an amount equivalent to that of the concentrated solution.

The centrifugal separation is preferably conducted at 200-20,000×g and the membrane filtration is preferably conducted so that the pressure is controlled to not more than 3.0 $kg/m^2$ with a MF membrane, a filter press, or the like. In the case of enzymes present in fungus bodies, it is preferred that the cells be ground in a homogenizer, a whirling blender, an ultrasonic grinder, a French press, a ball mill, or the like, and that the cell residues be removed by centrifugal separation, membrane filtration, or the like. The stirring rotation speed of the homogenizer is 500-30,000 rpm, preferably 1,000-15,000 rpm, the rotation speed of the whirling blender is 500-10,000 rpm, preferably 1,000-5,000 rpm. The stirring time is 0.5-10 min, preferably 1-5 min. The ultrasonic grinding may be conducted at 1-50 KHz, preferably 10-20 KHz. The ball mill may use small glass spheres with a diameter of about 0.1-0.5 mm.

In the present invention, it is preferred that a solution with a content of solids of 5-30 wt. % be used as the aqueous solution containing a lipase.

The fatty acid etc. is preferably added in an amount of 0.1-20 times, more preferably 0.3-10 times, and most preferably 0.3-5 times the weight of solids of the aqueous solution containing a lipase.

The concentration of solids in the aqueous solution containing a lipase can be found as Brix. % by using a sugar content meter (BRX-242, manufactured by CIS Co.).

After the fatty acid etc. has been added, the pH of the aqueous solution containing a lip ase may be adjusted to 10 or less, preferably to 6-10. The pH adjustment may be conducted immediately prior to drying, such as spray drying, but may be also conducted at any stage prior thereto. The pH of the aqueous solution containing a lipase may be adjusted in advance so that the pH immediately prior to the drying process be within the aforementioned range.

A variety of alkali agents or acids can be used for pH adjustment, but it is preferred that an alkali metal hydroxide such as sodium hydroxide be used.

In the process prior to drying, the aqueous solution containing a lipase may be concentrated. No specific limitation is placed on the concentration method, and concentration using an evaporator or a flash evaporator, UF membrane concentration, MF membrane concentration, salting out with inorganic salts, precipitation with a solvent, adsorption with an ion-exchange cellulose or the like, and water absorption with water-absorbing gel can be used. It is preferred that UF membrane concentration or evaporator be used. The module for UF membrane concentration is preferably a flat membrane or a hollow fiber membrane with a fraction molecular weight of 3,000-100,000, preferably 6,000-50,000, the material thereof preferably being a polyacrylonitrile, a polysulfone, or the like.

Spray drying may be carried out by using a spray drier of a nozzle countercurrent system, disk countercurrent system, nozzle concurrent flow system, disk concurrent flow system, or the like. It is preferred that spray drying be conducted with a disk concurrent flow system by controlling the atomizer rotation rate at 4,000-20,000 rpm and heating at an inlet temperature of 100-200° C. and an outlet temperature of 40-100° C.

Furthermore, it is also preferred that freeze drying be used. For example, it is preferred that freeze drying be conducted with a laboratory-size freeze drier for small quantities or a table-top freeze drier. The adjustment can be further conducted by vacuum drying.

When the lipase is a 1,3-specific lipase, in particular, a lipase derived from *Rhizomucor miehei* and *Alcaligenes* sp., 1,3-specificity becomes extremely high in accordance with the present invention, so that the lipase powder can be advantageously used as a lipase for transesterification. Furthermore, using this lipase powder makes it possible to conduct transesterification of oils and fats with good efficiency by the usual method.

Esterification can be also conducted by using the powdered lipase composition of the present invention. Here, compounds of a variety of types such as various monoalcohols, polyhydric alcohols, and aminoalcohols can be used as the compounds having at least one alcoholic hydroxyl group in a molecule which are subjected to the esterification. Specific examples include short-chain, medium-chain, and long-chain saturated, unsaturated, linear, and branched alcohols, glycerides, glycerin, erythritol, and other polyhydric alcohols. Among them, glycerin is preferred.

On the other hand, carboxylic acids can be short-chain, medium-chain, long-chain, saturated, unsaturated, linear, and branched carboxylic acids. Among them, fatty acids having 6 to 30 carbon atoms, for example, octanoic acid, decanoic acid, lauric acid, myristic acid, palmitic acid, stearic acid, oleic acid, linolic acid, and linoleic acid can be used. Those acids can be used individually or in combinations of two or more thereof. Unsaturated fatty acids are preferred and conjugated linolic acid is especially preferred.

As for esterification conditions, the reaction can be conducted, for example, according to the conditions described in Japanese Patent Applications Laid-open No H13-169795 or H15-113396. For example, the powdered lipase composition of the present invention may be added at 0.1-2 wt. % based on a total weight of the substrate, that is, based on a total weight of a carboxylic acid and a compound having an alcoholic hydroxyl group, and the reaction may be conducted for 24-72 hours at a temperature of 30-60° C. It is preferred that the reaction system be under reduced pressure and the reaction be conducted while removing water generated by esterification.

The present invention will be described below in more detail based on Examples of the present invention.

EXAMPLE 1

A liquid lipase (trade name Palatase) derived from *Rhizomucor miehei* (manufactured by Novo Nordisk Co., Ltd.) wherein lipase is dissolved or dispersed in an aqueous solution was treated with a UF module (SIP-0013, manufactured by Asahi Chemical Industries Co., Ltd.) to remove low-molecular weight components and a lipase-containing aqueous solution 1 (concentration of solids of 20.1 wt. %) was obtained. More specifically, the liquid lipase (Palatase) was UF membrane treated under ice cooling and concentrated to ½ volume thereof, and a 0.01 M phosphoric acid buffer with pH 7 was then added in an amount equal to that of the concentrate.

The operation of adding a phosphoric acid buffer after the UF membrane treatment was then repeated twice with respect to the solution obtained, and then the UF membrane treatment was further conducted to convert the obtained lipase concentrate into a lipase-containing aqueous solution 1.

A total of 20 ml of water and 40 ml of aqueous suspension of fatty acid monoglyceride (3 wt. % aqueous suspension of n-decanoic acid monoglyceride (C10MAG)) were added to 20 ml of the lipase-containing aqueous solution 1. The pH of the solution thus obtained was adjusted to pH 9.1 by using an aqueous solution of sodium hydroxide.

A lipase powder was obtained by spraying this solution with a spray drier (SD-1000, manufactured by Tokyo Rika Kikai Co.) under the following conditions: inlet temperature 130° C., dry air flow rate 0.7-1.1 m$^3$/min, and spraying pressure 11-12 kPa. The particles of the lipase powder had a spherical shape, 90 wt. % or more of the lipase powder had a particle size within a range of 1-100 µm, and the mean particle size was 7.6 µm. The particle size was measured using a particle size distribution meter (LA-500) manufactured by HORIBA Co.

The concentration of solids in the lipase-containing aqueous solution 1 was found as Brix. % by using a sugar content meter (BX-242, manufactured by CIS Co.).

EXAMPLE 2

A lipase powder was obtained in the same manner as in Example 1, except that an aqueous suspension of a fatty acid (5 wt. % aqueous suspension of n-decanoic acid (C10FA)) was used in place of the aqueous suspension of fatty acid monoglycerides (3 wt. % aqueous suspension of n-decanoic acid).

COMPARATIVE EXAMPLE 1

A lipase powder was obtained in the same manner as in Example 1, except that the lipase concentrate and the 0.01 M phosphoric acid buffer with pH 7 were used at a volume ratio of 1:1.

Lipase activity of the lipase powders thus obtained was measured by the method described below. The results are shown in Table 1.

Lipase Activity

A powdered lipase was added to an oil obtained by mixing triolein and tricaprylin at a ratio of 1:1 (w) and the reaction was conducted at 60° C. A total of 10 µl was sampled and diluted with 1.5 ml of hexane. The powdered lipase was then filtered and the solution obtained was used as a sample for gas chromatography. Analysis was conducted by gas chromatography (column: DB-1 ht) and the reaction ratio was found by the following formula. The gas chromatography conditions were as follows: initial column temperature 150° C., temperature rise rate 15° C./min, finish temperature 370° C. Other conditions were identical to the below-described 1,3-selectivity test.

Reaction ratio (%)={C34 area/(C24 area+C34 area)}× 100.

In the formula, C24 is tricaprylin, C34 is a compound in which one fatty acid of tricaprylin is substituted with C 18; area is the area size thereof.

The values of reaction rate constant K were found by analytical software (Orijin ver. 6.1) based on the reaction ratio in each time interval. The lipase activity was represented by a relative activity, with the K value of the Comparative Example 1 taken as 100.

TABLE 1

| Conditions (volume ratio) | Relative activity |
| --- | --- |
| Comparative Example 1. Lipase concentrate:bf(7) = 1:1 | 100 |
| Example 1. Lipase concentrate:water:C10MAG = 0.5:0.5:1 | 659 |
| Example 2. Lipase concentrate:water:C10FA = 0.5:0.5:1 | 964 |

EXAMPLE 3

A total of three aqueous suspensions of fatty acids were used: suspension 1 (5 wt. % aqueous suspensions of n-octanoic acid (C8FA)), suspension 2 (5 wt. % aqueous solution of n-decanoic acid (C10FA)), and suspension 3 (5 wt. % aqueous suspension of n-dodecanoic acid (C12FA)), and lipase powders were obtained in the same manner as in Example 2, except that half of the those fatty acids was neutralized with NaOH (pH 6.8) with respect to the aqueous solutions obtained.

The lipase activity of the lipase powders thus obtained was measured by the above-described method. The results are shown in Table 2 together with the results relating to Comparative Example 1.

TABLE 2

| Conditions (volume ratio) | Relative activity |
| --- | --- |
| Comparative Example 1 | 100 |
| Suspension 1 (C8FA) | 463 |
| Suspension 2 (C10FA) | 667 |
| Suspension 3 (C12FA) | 310 |

What is claimed is:

1. A lipase powder which is a granulated material consisting essentially of a 1,3-specific lipase derived from *Rhizomucor miehei* and at least one member selected from the group consisting of saturated fatty acids having 8 to 12 carbon atoms, monoglycerides thereof, diglycerides thereof, and a mixture thereof, wherein said lipase powder is obtained by:
adding said fatty acids, monoglycerides, diglycerides, or mixtures thereof said lipase; and, granulating and powdering the lipase.

2. The lipase powder according to claim 1, which is obtainable by adding at least one member selected from the group consisting of saturated fatty acids having 8 to 12 carbon atoms, monoglycerides thereof, diglycerides thereof, and a mixture thereof to an aqueous solution containing a lipase and spray-drying or freeze-drying the resulting solution.

3. The lipase powder according to claim 2, wherein the pH of the aqueous solution containing a lipase is adjusted to 6-10 after at least one member selected from the group consisting of saturated fatty acids having 8 to 12 carbon atoms, monoglycerides thereof, diglycerides thereof, and a mixture thereof is added thereto.

4. The lipase powder according to claim 1, where 90 wt.% or more of the lipase powder has a particle size of 1-100 μm.

5. A lipase powder of claim 1 for use in esterification or transesterification.

6. The lipase powder according to claim 1, wherein the at least one member selected from the group consisting of saturated fatty acids having 8 to 12 carbon atoms, monoglycerides thereof, diglycerides thereof, and a mixture thereof is fatty acid monoglyceride (C10MAG).

7. The lipase powder according to claim 1, wherein the moisture content of the lipase powder is 10 wt.% or less.

8. The lipase powder according to claim 7, wherein the moisture content is from 6.5-8.5 wt.%.

* * * * *